US011260943B2

United States Patent
Kartalov et al.

(10) Patent No.: US 11,260,943 B2
(45) Date of Patent: Mar. 1, 2022

(54) IMPLANTABLE MICRO-SENSOR TO QUANTIFY DISSOLVED INERT GAS

(71) Applicant: CALIFORNIA INSTITUTE OF TECHNOLOGY, Pasadena, CA (US)

(72) Inventors: Emil P. Kartalov, Monterey, CA (US); Axel Scherer, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 126 days.

(21) Appl. No.: 16/719,371

(22) Filed: Dec. 18, 2019

(65) Prior Publication Data

US 2020/0216155 A1 Jul. 9, 2020

Related U.S. Application Data

(60) Provisional application No. 62/790,151, filed on Jan. 9, 2019.

(51) Int. Cl.
*B63C 11/02* (2006.01)
*G01N 27/22* (2006.01)
*G01N 21/41* (2006.01)

(52) U.S. Cl.
CPC .............. *B63C 11/02* (2013.01); *G01N 21/41* (2013.01); *G01N 27/221* (2013.01)

(58) Field of Classification Search
CPC ....... B63C 11/02; G01N 21/41; G01N 27/221
USPC ....................................................... 405/186
See application file for complete search history.

(56) References Cited

U.S. PATENT DOCUMENTS

| | | | | |
|---|---|---|---|---|
| 5,514,253 A | * | 5/1996 | Davis et al. | G01N 27/404 205/782.5 |
| 6,234,004 B1 | * | 5/2001 | Revsbech et al. | G01F 1/34 73/19.04 |
| 6,408,679 B1 | * | 6/2002 | Kline-Schoder et al. | A61B 8/08 73/19.03 |
| 7,313,482 B2 | * | 12/2007 | Drlica et al. | G16B 20/00 702/19 |
| 7,313,483 B2 | | 12/2007 | Crow et al. | |

(Continued)

FOREIGN PATENT DOCUMENTS

| WO | 2017/027643 A1 | 2/2017 |
|---|---|---|
| WO | 2020/146106 A1 | 7/2020 |

OTHER PUBLICATIONS

International Preliminary Report on Patentability for International Application No. PCT/US2019/067170 filed on Dec. 18, 2019, on behalf of California Institute of Technology, dated Jul. 22, 2021. 10 Pages.

(Continued)

*Primary Examiner* — Tara Mayo-Pinnock
(74) *Attorney, Agent, or Firm* — Steinfl + Bruno, LLP

(57) ABSTRACT

Methods and devices including implantable micro-sensors used to detect tissue-dissolved inert gas and to detect microbubble formation to avoid Caisson disease are described. The disclosed methods and devices are based on measuring the refractive index changes in hydrophobic liquids after absorbing an inert gas such as nitrogen. The changes in the refractive index are based on implementing one of an interferometry, optical microcavity resonance shift, a photonic crystal resonance, a beam deflection, a resonance tuning or detuning, an amplitude change, or an intensity change method.

17 Claims, 2 Drawing Sheets

(56) References Cited

U.S. PATENT DOCUMENTS

| | | | |
|---|---|---|---|
| 7,613,491 B2* | 11/2009 | Boock et al. | A61B 5/14532 600/347 |
| 2014/0148710 A1* | 5/2014 | Holopainen et al. | A61B 5/01 600/483 |
| 2018/0156775 A1* | 6/2018 | Chou et al. | A61B 5/0935 |

OTHER PUBLICATIONS

International Search Report and Written Opinion for International Application No. PCT/US2019/067170 filed on Dec. 18, 2019 on behalf of California Institute of Technology, dated Apr. 14, 2020. 15 Pages.

* cited by examiner

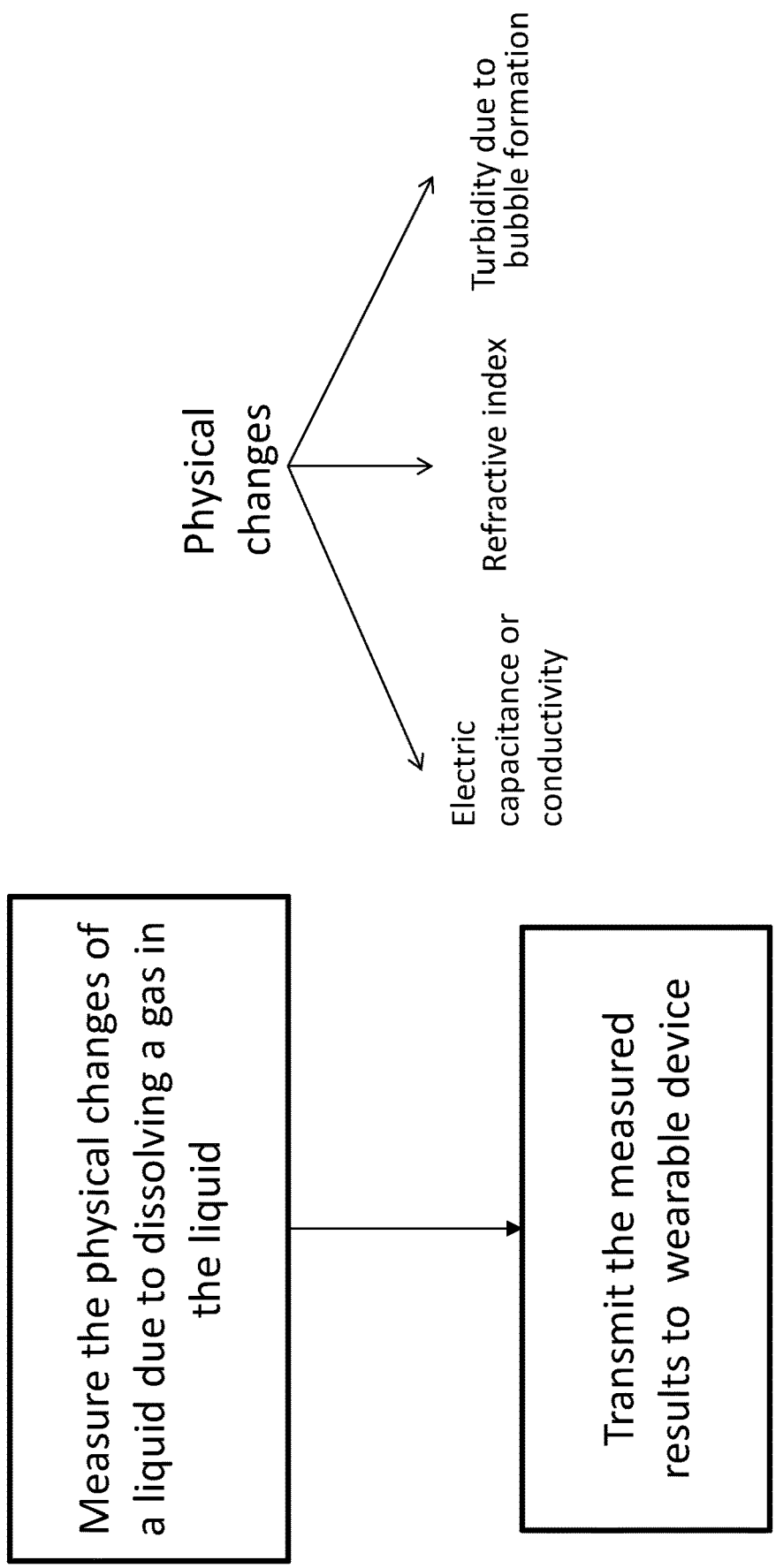

IMPLANTABLE MICRO-SENSOR TO QUANTIFY DISSOLVED INERT GAS

CROSS REFERENCE TO RELATED APPLICATIONS

The present application claims priority to U.S. Provisional Application 62/790,151 filed on Jan. 9, 2019, the contents of which are incorporated herein by reference in their entirety.

FIELD

The presented disclosure is related to micro-sensors, in particular implantable micro-sensors to quantify dissolved inert gas, and more particularly to implantable micro-sensors used to detect tissue-dissolved nitrogen and to detect microbubble formation to avoid e.g. Caisson disease.

BACKGROUND

Throughout this document the term "tissue-dissolved" will refer to "dissolved in tissue", with particular reference to the biological tissue of the diver.

Caisson disease (known also as "the bends") is a potentially lethal health risk for divers breathing a nitrogen gas mixture. As pressure increases with depth, nitrogen dissolves in the tissues of the diver. When the diver ascends, the positive pressure difference stimulates bubble formation in the tissues and blood vessels, potentially causing serious tissue damage, embolism, and possibly death. Generally, the reason for breathing mixtures to contain an inert gas is because pure oxygen is toxic as it is highly reactive and will burn tissues. In the atmosphere, oxygen is diluted by nitrogen, therefore human lungs can withstand it. A diver generally requires a similar setup. For simple shallow dives, divers usually use compressed air, which is inexpensive and already comes at the necessary ratio between oxygen and an inert gas. For deeper dives, divers use more complex mixtures of other inert gasses, e.g. helium. However, any inert gas that does not have its own biological system of efficient transport through the blood (as oxygen and carbon dioxide have through hemoglobin binding) will produce the same or similar decompression problem.

To help avoid these risks, divers time the ascent in accordance with diving charts, to allow for the excess nitrogen to be exhaled safely. However, the charts are only approximate, while biological variability and the relative randomness of bubble formation produce significant uncertainty. Moreover, slow ascent might be impracticable in cold environments, hostile waters, or clandestine missions. Slow ascent might also be undesirable in emergencies.

SUMMARY

The teachings of the present disclosure address the problems described in the previous section and provide methods to measure the concentration of nitrogen dissolved in tissues and monitor microbubble formation. The described methods and devices may also use the output of that measurement in combination with diving charts and depth information to form a "diving solution" recommendation to the diver in real time using a handheld/wearable monitor.

The property of nitrogen and other inert gases to preferentially absorb into hydrophobic environments is known to the person skilled in the art. This property is known as part of the current understanding of the mechanism of nitrogen narcosis, where nitrogen dissolves in the cell membranes, which are made of a double layer of lipids. The disclosed devices and methods use such property to build implantable sensors.

Further aspects of the disclosure are provided in the description, drawings and claims of the present application.

According to a first aspect of the present disclosure, a sensor is provided, comprising: a micro-chamber capsule filled with a hydrophobic liquid; and a measurement unit connected with the micro-chamber capsule; wherein the measurement unit is configured to: detect and quantify a concentration of an inert gas by measuring a physical change of the hydrophobic liquid due to a dissolving of the inert gas in the hydrophobic liquid; and generate measured results.

According to a second aspect of the present disclosure, a method of detecting and quantifying a concentration of an inert gas dissolved in a hydrophobic liquid is disclosed, providing: measuring a physical change of the hydrophobic liquid due to the dissolving of the inert gas in the hydrophobic liquid; and providing measured results including the concentration of the inert gas.

According to a third aspect of the present disclosure, a method of detecting and quantifying microbubble formation of an inert gas dissolved in a hydrophobic liquid, comprising: measuring a physical change of the hydrophobic liquid due to the dissolving of the inert gas in the hydrophobic liquid; and providing measured results including the concentration of the inert gas.

DESCRIPTION OF THE DRAWINGS

FIG. 2A shows a flowchart illustrating methods according to the teachings of the present disclosure FIG. 2B shows examples of physical changes in a hydrophobic liquid after absorbing an inert gas such as nitrogen.

DETAILED DESCRIPTION

Figure 1:
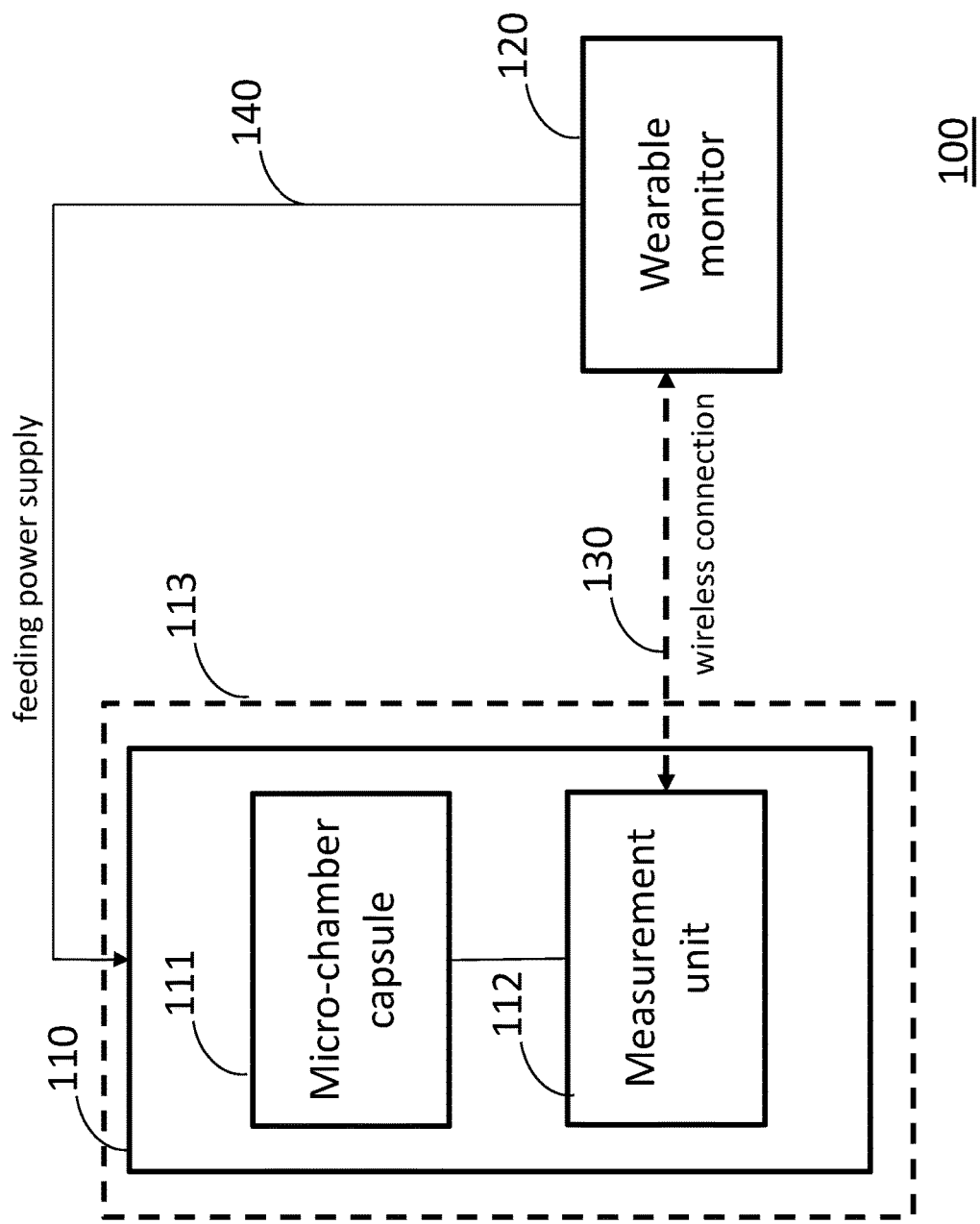
FIG. 1 shows an electronic system according an exemplary embodiment of the present disclosure.

FIG. 1 shows an electronic system (100) comprising a sensor (110) and a wearable monitor (120) in accordance with an embodiment of the present disclosure. The implantable sensor (110) comprises a micro-chamber capsule (111). Throughout this document the term "capsule" will mean "enclosed chamber". In accordance with a further embodiment of the present disclosure, the measured data may be transmitted wirelessly from the measurement unit (112) to the wearable monitor (120), as shown by the arrow (130). The wearable monitor (120) may provide power to the implantable sensor (110) as shown by the arrow (140). Dimensions of the micro-chamber capsule may be on the scale of microns, tens of microns or hundreds of microns. As also shown in FIG. 1, the sensor (110) may optionally be implemented on a microchip (113)

In accordance with the teachings of the present disclosure, the micro-chamber (111) may be filled by a hydrophobic liquid such as lipid, gel, or oil. Physical properties of the hydrophobic liquid may change due to absorption of an inert gas such as nitrogen, helium, neon, krypton, argon, or a mixture thereof. The change of such physical properties is then detected and measured by measurement unit (112) by using for example electronic or interferometric techniques. Moreover, the change in physical properties of the liquid due to the absorption of the gas (e.g. nitrogen) can then be calibrated within the measurement unit and with known nitrogen concentration. In what follows, the disclosed concept will be described more in detail and through some exemplary embodiments.

As an example, absorption of nitrogen would change the refractive index of the working liquid. In an exemplary embodiment, interferometric techniques may be used to detect and measure the changes in the refractive index. These techniques have been shown to be miniaturizable, particularly with the use of photonic crystals, Bloch arrays, and the use of optical micro-cavities etc. In accordance with further embodiments of the present disclosure, to help miniaturization, the actual detection may be set up to be looking for a tuning or detuning shift of preset magnitude. Other embodiments in accordance with the present disclosure may be envisaged where an array of sensors such as the implantable sensor (110) of FIG. 1 are implemented in a microchip where an overall calibration may be performed by varying the shift across the array. The change in the refractive index may be measured using various techniques such as interferometry, Optical microcavity resonance shift, photonic crystal resonance, beam deflection, resonance tuning or detuning, amplitude change, or intensity change.

In an alternative embodiment in accordance with the present disclosure, the measurement unit (112) comprises micro-fabricated and micro-patterned electrodes to measure the electrical capacitance or conductivity in the micro-chamber capsule (111) to detect the absorbed gas (e.g. nitrogen). Using micro-fabricated and micro-patterned electrodes improves the sensitivity of measurements. Absorption of nitrogen would provide additional diatomic molecules to the liquid (acting as a dielectric) within the micro-chamber capsule (111), additional diatomic molecules being subject to dielectric polarization when an electric field is applied. The change in dielectric constant can then be measured by the measurement unit (112). This effect can be amplified by adding metallic particles to the micro-chamber material. As the hydrophobic material is compressed or expands with the introduction of inert gas, the metallic particles change the conductivity of the metal/polymer composite, and change the measured capacitance or conductivity that is measured.

According to embodiments of the present disclosure, the measurement unit (112) may be made based on optical measurements of turbidity to detect the onset of microbubble formation. In the absence of bubbles, the liquid (e.g. lipid or oil) inside the micro-capsule (111) is optically clear. When microbubbles start forming, they would act as optical scatterers increasing the apparent turbidity of the liquid. Alternatively, the optical measurement may be based on a reflection, which will turn from specular to diffusive when the microbubbles start forming. Both techniques may be implemented based on an intensity measurement, which is known to be easily miniaturizable. Other embodiments in accordance with the present disclosure may also be made wherein the microbubble formation is detected by measuring the electrical conductivity and/or capacitance of the liquid inside the micro-chamber capsule (111). In such a case, the measurement unit (112) comprises, preferably, micro-fabricated and micro-patterned electrodes. The formation of the bubbles will displace the dielectric liquid away from the electrodes, thereby lowering capacitance and/or conductivity of the system, depending on what liquid is used.

FIG. 2A shows a general flowchart (200) illustrating the disclosed methods where first a physical change due to absorption of a gas in a liquid is detected and measured, and the measured results are then transmitted to a wearable device. Examples of such physical changes are summarized in FIG. 2B. Various exemplary electrical and optical techniques that can be used to measure such changes were described in the previous paragraphs.

Referring back to FIG. 1, the electronic system (100) can be used to improve safety and efficiency of diving operations. During a diving operation, the wearable monitor (120) may be worn by the diver, and the implantable sensor (110) is implanted or injected in the diver's body. As an example, a small incision can be made in the skin and the microchip is inserted in the incision under the skin. The incision is sufficiently small such that the skin can just be glued closed (no stitches required). Alternatively, the device can be miniaturized to fit through an injection needle, and inserted into the subdermal space underneath the reader. The recovery is very quick (full heal within a week) due to the small size of the incision. The wearable monitor (120) communicates wirelessly with the implantable sensor (110) to provide diver with the measured results. According to various embodiments of the present disclosure:

- Power is supplied to the implantable sensor (110) by the wearable monitor (120) through electromagnetic induction.
- The implantable sensor (110) is fabricated on a microchip.
- The wearable monitor (120) may use the received measured results from the implantable sensor (110) to provide visual or sonic feedback to the diver or the user wearing the wearable monitor (120).
- The wearable monitor (120) may be a handheld device.
- The wearable monitor can be part of a health-monitoring system that includes other sensors and provides integrated output to external monitoring systems. The wearable monitor may be connected to that system wirelessly or by wire as part of a wearable biomedical suit.
- Measuring the nitrogen concentration e.g. by the measurement unit seeing a shift in the absorption maximum may be independent of using turbidity to measure microbubble formation. The nitrogen concentration can be converted into partial pressure and compared to the ambient pressure to produce a risk assessment of bubble formation, with its own three zones defined (green, yellow, red). Low risk may be represented as "green status". Higher risk may be represented as "yellow" or "red" to the diver.
- The microbubble turbidity measurement can independently indicate if bubbles are formed or not. That is a "yes/no" measurement in general, but some calibration may be performed to graduate it into zones if desired, e.g. based on the quantification of the measured turbidity and some calibration to the severity of microbubble formation.
- Both measurement (inert gas concentration) and bubble turbidity may be implemented on the same chip with both outputs transmitted to the wearable device to display.
- The measured data may be combined with preprogrammed diving charts and measured depth to calculate the best plan for ascent and change it dynamically as new data is received in real time. Further biometrics may also be tied in.
- The measured data may be calibrated offline without involvement of the diver and then used in real time. This is performed by applying a known ambient pressure and concentration of the inert gas (e.g. nitrogen), then waiting for equilibration followed by performing titrated measurements to be used to calibrate the measured data.

What is claimed is:

1. A sensor comprising:
    a micro-chamber capsule filled with a hydrophobic liquid; and
    a measurement unit connected with the micro-chamber capsule;
    wherein the measurement unit is configured to:
        detect and quantify a concentration of an inert gas by measuring a physical change of the hydrophobic liquid due to a dissolving of the inert gas in the hydrophobic liquid,
        generate measured results;
        the physical change is a change in a refractive index of the hydrophobic liquid, and the measurement unit measures the change in the refractive by implementing one of an interferometry, optical microcavity resonance shift, a photonic crystal resonance, a beam deflection, a resonance tuning or detuning, an amplitude change, or an intensity change method.

2. The sensor of claim 1, wherein the hydrophobic liquid comprises one of lipid, gel, or oil.

3. The sensor of claim 1, wherein the inert gas comprises one of nitrogen, helium, neon, krypton, argon, or a mixture thereof.

4. The sensor of claim 3, wherein dimensions of the micro-chamber capsule are on a scale of microns, tens of microns, or hundreds of microns.

5. The sensor of claim 4, wherein the sensor is implantable in animal or human subjects.

6. An electronic system comprising a sensor and a wearable monitor, the sensor comprising:
    a micro-chamber capsule filled with a hydrophobic liquid; and
    a measurement unit connected with the micro-chamber capsule,
    wherein:
        the measurement unit is configured to detect and quantify a concentration of an inert gas by measuring a physical change of the hydrophobic liquid due to a dissolving of the inert gas in the hydrophobic liquid, and generate measured results;
        the measurement unit is configured to communicate with and transmit the measured results to the wearable monitor;
        the sensor in inductively powered by the wearable monitor;
        the inert gas comprises one of nitrogen, helium, neon, krypton, argon, or a mixture thereof;
        dimensions of the micro-chamber capsule are on a scale of microns, tens of microns, or hundreds of microns, and
        the sensor is implantable in animal or human subjects.

7. A method of detecting and quantifying a concentration of an inert gas dissolved in a hydrophobic liquid, comprising:
    measuring a physical change of the hydrophobic liquid due to the dissolving of the inert gas in the hydrophobic liquid; and
    providing measured results including the concentration of the inert gas,
    wherein the physical change is a change in a refractive index of the hydrophobic liquid, and the measuring comprises implementing one of an interferometry, optical microcavity resonance shift, a photonic crystal resonance, a beam deflection, a resonance tuning or detuning, an amplitude change, or an intensity change method.

8. The method of claim 7, wherein the hydrophobic liquid comprises one of lipid, gel, or oil and wherein the inert gas comprises one of nitrogen, helium, neon, krypton, argon, or a mixture thereof.

9. A method of detecting and quantifying a concentration of an inert gas dissolved in a hydrophobic liquid, comprising:
    applying the inert gas with a known ambient pressure and a known concentration to the hydrophobic liquid, the hydrophobic liquid comprising one or lipid, gel or oil, and the inert gas comprising one of nitrogen, helium, neon, krypton, argon, or a mixture thereof;
    waiting for equilibration;
    taking titrated measurements of a physical change of the hydrophobic liquid due to the dissolving of the inert gas in the hydrophobic liquid, thereby calibrating the measured results in real time; and
    providing measured results including the concentration of the inert gas.

10. The method of claim 9, further comprising wirelessly transmitting the measured results to a wearable monitor; and displaying the measured results by the wearable monitor.

11. The method of claim 10, further comprising:
    filling a micro-chamber placed in a micro-chip with the inert gas;
    implement the measuring on the micro-chip;
    implanting the micro-chip in a body of a diver wearing the variable monitor; and
    combining the measured results with a pre-programmed diving chart saved in the wearable monitor to generate a diving plan for the diver.

12. A method of detecting and quantifying microbubble formation of an inert gas dissolved in a hydrophobic liquid, comprising:
    measuring a physical change of the hydrophobic liquid due to the dissolving of the inert gas in the hydrophobic liquid; and
    providing measured results including the concentration of the inert gas,
    wherein the physical change is a change in a refractive index of the hydrophobic liquid, and the measuring comprises implementing one of an interferometry, optical microcavity resonance shift, a photonic crystal resonance, a beam deflection, a resonance tuning or detuning, an amplitude change, or an intensity change method.

13. The method of claim 12, wherein the hydrophobic liquid comprises one of lipid, gel, or oil and wherein the inert gas comprises one of nitrogen, helium, neon, krypton, argon, or a mixture thereof.

14. A method of detecting and quantifying microbubble formation of an inert gas dissolved in a hydrophobic liquid, comprising:
    measuring a physical change of the hydrophobic liquid due to the dissolving of the inert gas in the hydrophobic liquid, the hydrophobic liquid comprising one of lipid, gel, or oil and the inert gas comprising one of nitrogen, helium, neon, krypton, argon, or a mixture thereof; and
    providing measured results including the concentration of the inert gas,
    wherein the physical change is a change in turbidity and the measuring comprises applying light to the hydrophobic liquid and quantifying one of:
        a) an intensity of the light;
        b) an increased scattering of the light;
        c) a switching from specular to diffusion of the light;
        d) a shift in a reflection of the light; and
        e) a shift in refraction of the light.

and wherein the hydrophobic liquid comprises one of lipid, gel, or oil and wherein the inert gas comprises one of nitrogen, helium, neon, krypton, argon, or a mixture thereof.

15. A method of detecting and quantifying microbubble formation of an inert gas dissolved in a hydrophobic liquid, comprising:
- measuring a physical change of the hydrophobic liquid due to the dissolving of the inert gas in the hydrophobic liquid, the hydrophobic liquid comprising one of lipid, gel, or oil and the inert gas comprising one of nitrogen, helium, neon, krypton, argon, or a mixture thereof;
- providing measured results including the concentration of the inert gas, and
- wirelessly transmitting the measured results to a wearable monitor; and displaying the measured results by the wearable monitor.

16. The method of claim 15, further comprising:
- implementing the micro-chamber and the measuring on a micro-chip;
- filling the micro-chamber with the inert gas;
- implanting or injecting the micro-chip in a body of a diver wearing the wearable monitor; and
- combining the measured results with a pre-programmed diving chart saved in the wearable monitor to generate a diving plan for the diver.

17. The method of claim 16, wherein the injecting is performed into a subdermal space underneath the wearable monitor.

* * * * *

UNITED STATES PATENT AND TRADEMARK OFFICE
CERTIFICATE OF CORRECTION

PATENT NO. : 11,260,943 B2  
APPLICATION NO. : 16/719371  
DATED : March 1, 2022  
INVENTOR(S) : Emil P. Kartalov et al.

Page 1 of 1

It is certified that error appears in the above-identified patent and that said Letters Patent is hereby corrected as shown below:

In the Claims

In Column 5, Line 11 (Claim 1), add the word "and" after the phrase "hydrophobic liquid,"

In Column 5, Lines 15-16 (Claim 1), add the word "index" between the phrase "measures the change in the refractive" and "by implementing one of an interferometry, optical microcavity"

In Column 5, Lines 45-46 (Claim 6), replace "in" with "is" in the phrase "the sensor in inductively powered by the wearable monitor;"

In Column 6, Line 26 (Claim 11), replace "implement" with "implementing" in the phrase "implement the measuring on the micro-chip;"

Signed and Sealed this  
Ninth Day of August, 2022

Katherine Kelly Vidal  
*Director of the United States Patent and Trademark Office*